(12) United States Patent
Bard

(10) Patent No.: US 8,961,443 B2
(45) Date of Patent: Feb. 24, 2015

(54) INFLATABLE CERVICAL TRACTION DEVICE

(75) Inventor: Maurice Bard, Markham (CA)

(73) Assignee: IWI Ltd., Markham, ON (CA)

(*) Notice: Subject to any disclaimer, the term of this patent is extended or adjusted under 35 U.S.C. 154(b) by 148 days.

(21) Appl. No.: 13/353,815

(22) Filed: Jan. 19, 2012

(65) Prior Publication Data

US 2012/0259260 A1    Oct. 11, 2012

(30) Foreign Application Priority Data

Apr. 7, 2011  (CA) .................................... 2736654

(51) Int. Cl.
  *A61F 5/00*   (2006.01)
  *A61F 5/055*  (2006.01)
  *A61F 5/058*  (2006.01)

(52) U.S. Cl.
  CPC ............. *A61F 5/05816* (2013.01); *A61F 5/055* (2013.01)
  USPC .............................................. 602/36; 602/38

(58) Field of Classification Search
  USPC ................. 602/17–19, 32, 34–36, 40, 61, 74; 5/622–624, 636–637, 708, 644; 601/6; 128/DIG. 19, DIG. 20, DIG. 23, 128/845–870, 97.1
  See application file for complete search history.

(56) References Cited

U.S. PATENT DOCUMENTS

| | | | | |
|---|---|---|---|---|
| 35,113 | A * | 4/1862 | Grim | 254/269 |
| 3,885,403 | A * | 5/1975 | Spencer | 62/530 |
| 3,901,225 | A * | 8/1975 | Sconce | 602/13 |
| 5,402,535 | A * | 4/1995 | Green | 2/468 |
| 5,407,421 | A * | 4/1995 | Goldsmith | 602/5 |
| 7,070,573 | B2 * | 7/2006 | Axelsson | 602/18 |
| 2003/0120192 | A1 * | 6/2003 | Chao | 602/36 |
| 2003/0158015 | A1 * | 8/2003 | Watson | 482/10 |

* cited by examiner

*Primary Examiner* — Ophelia A Hawthorne

(57) ABSTRACT

A cervical traction device advantageously includes a therapeutic pack that can be separately heated or chilled for use with the device. The most common application is a cold pack insertable in a recessed pocket of the device to provide cold therapy as the device is inflated during cervical decompression. The structure preferably includes a series of bladders that cooperate to define a cavity for accepting the therapeutic pack on an inside surface for thermal exchange with the neck of a user.

8 Claims, 7 Drawing Sheets

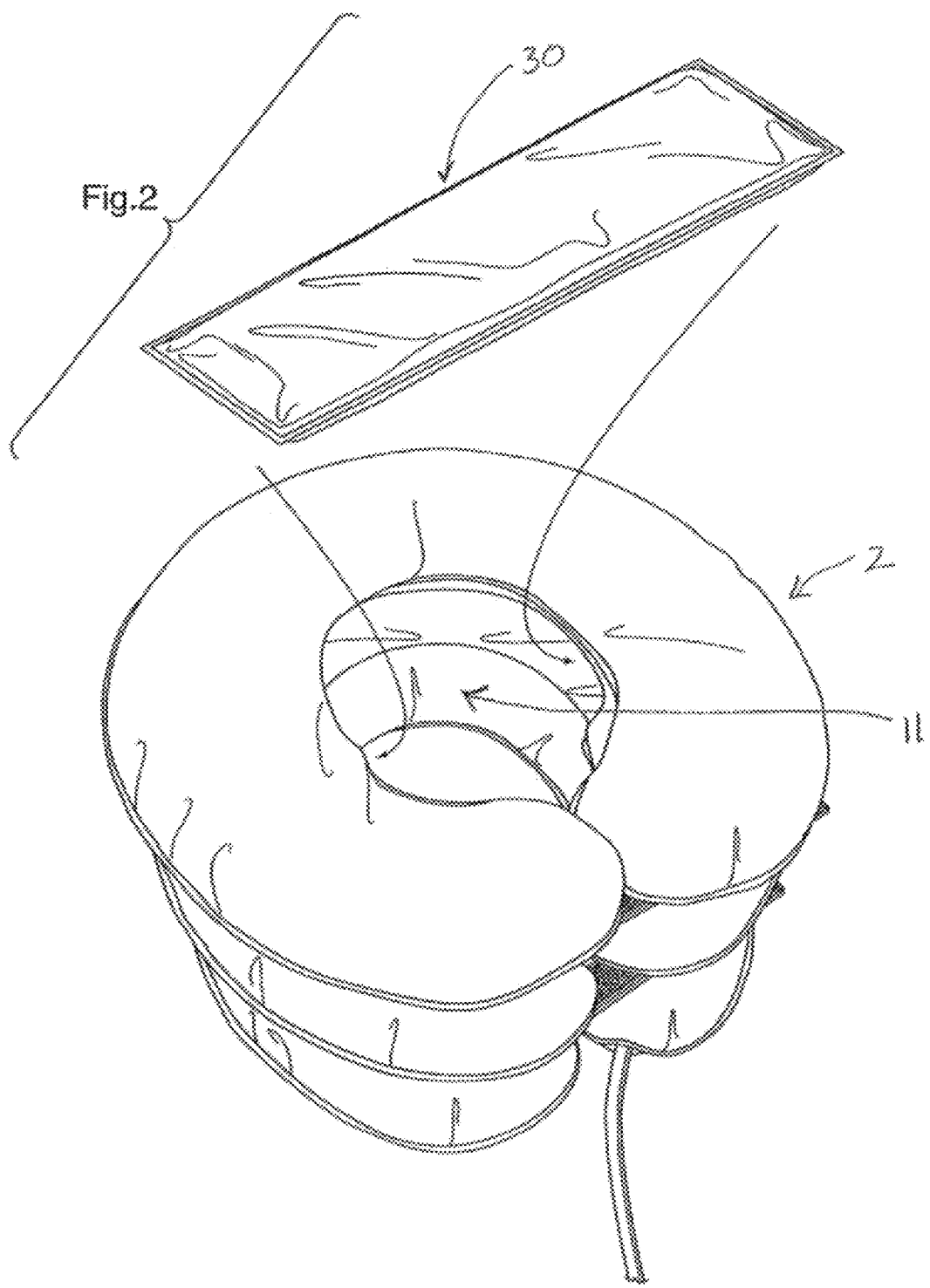

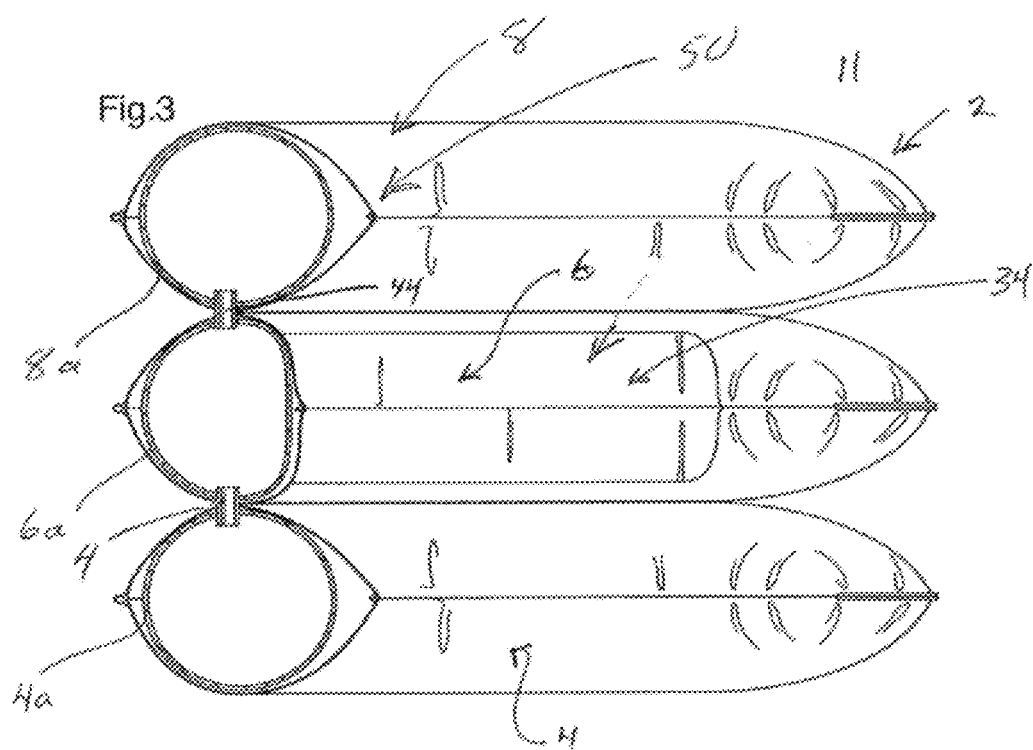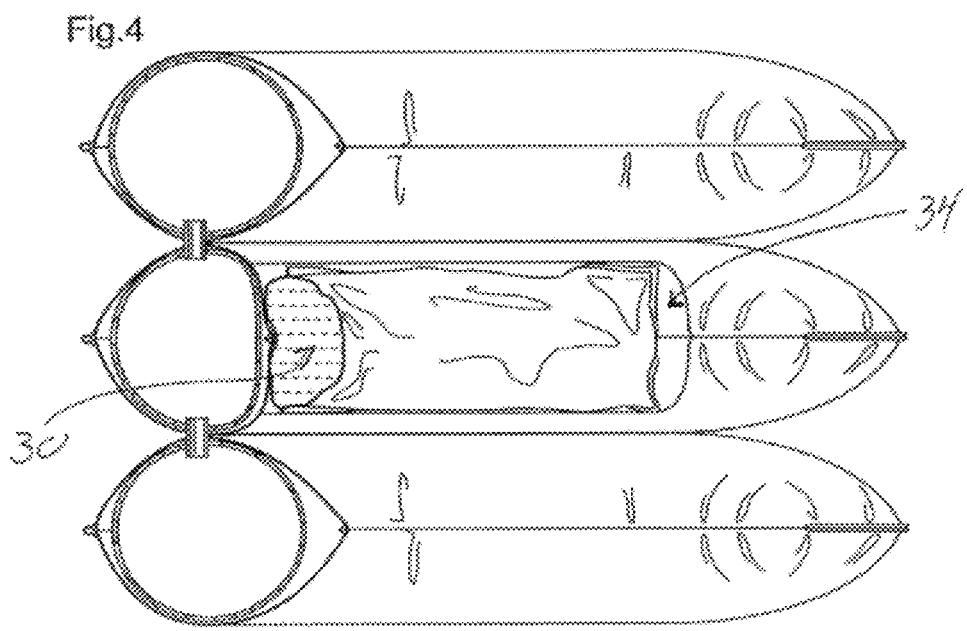

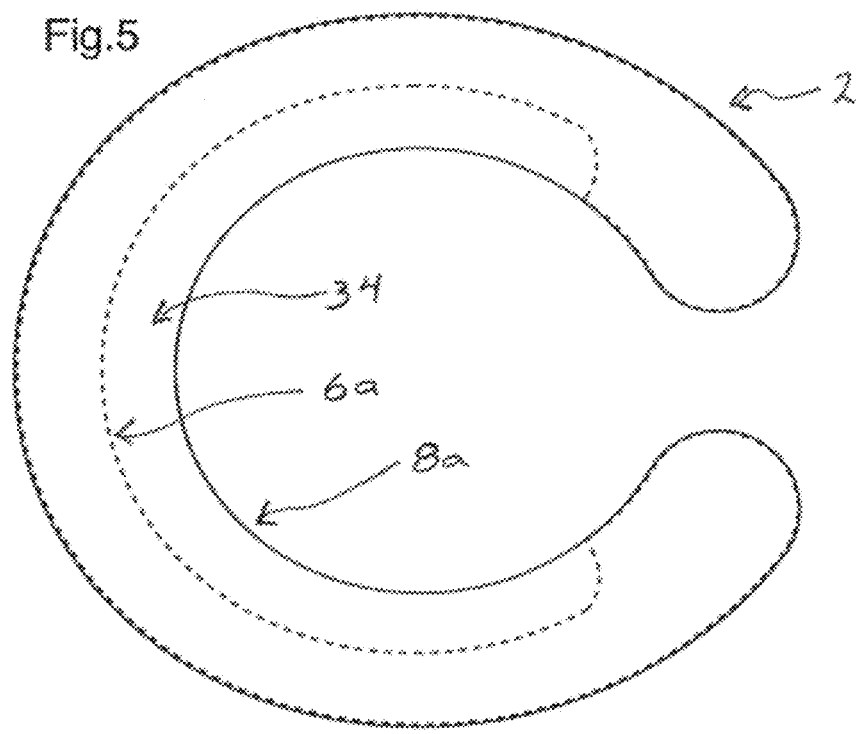
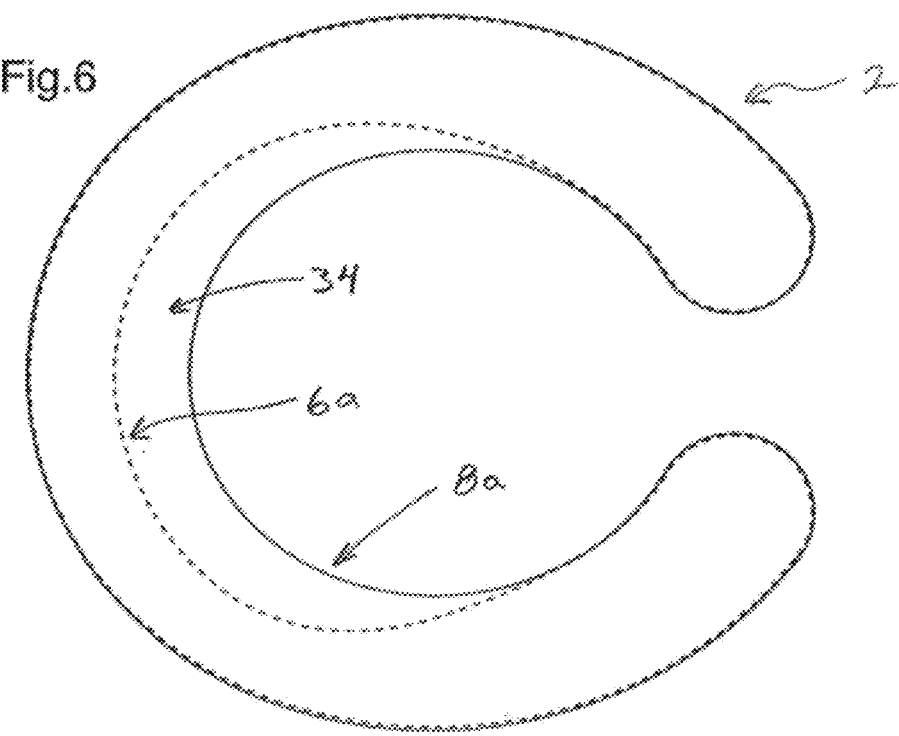

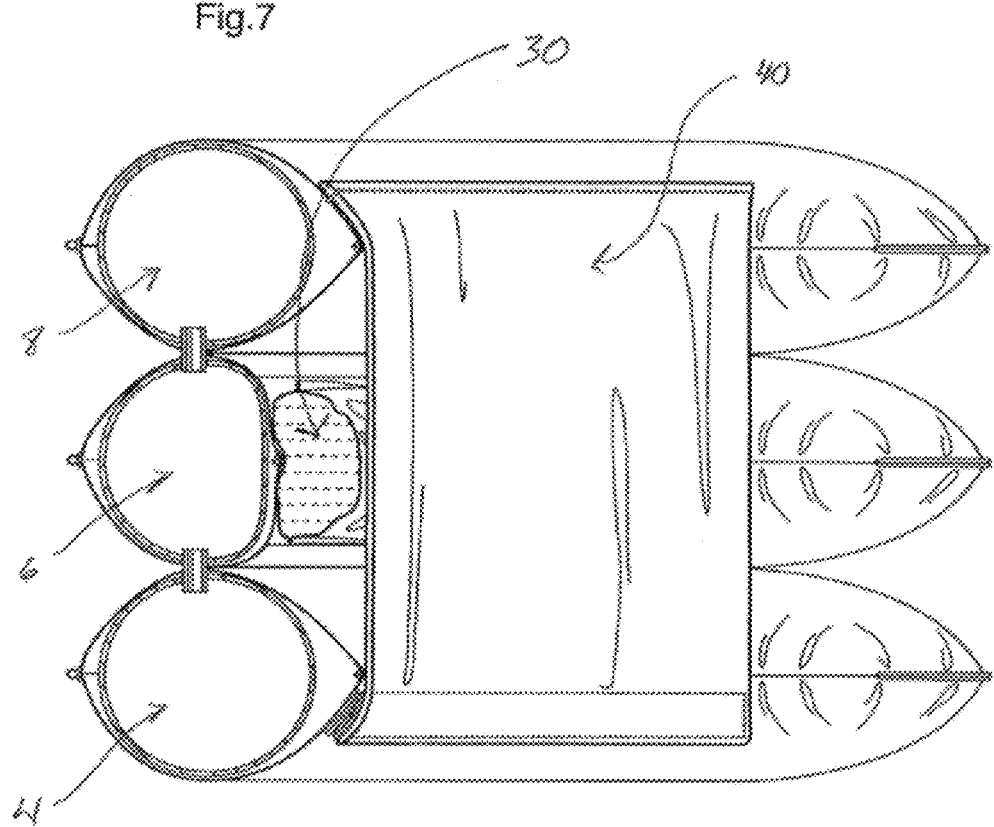

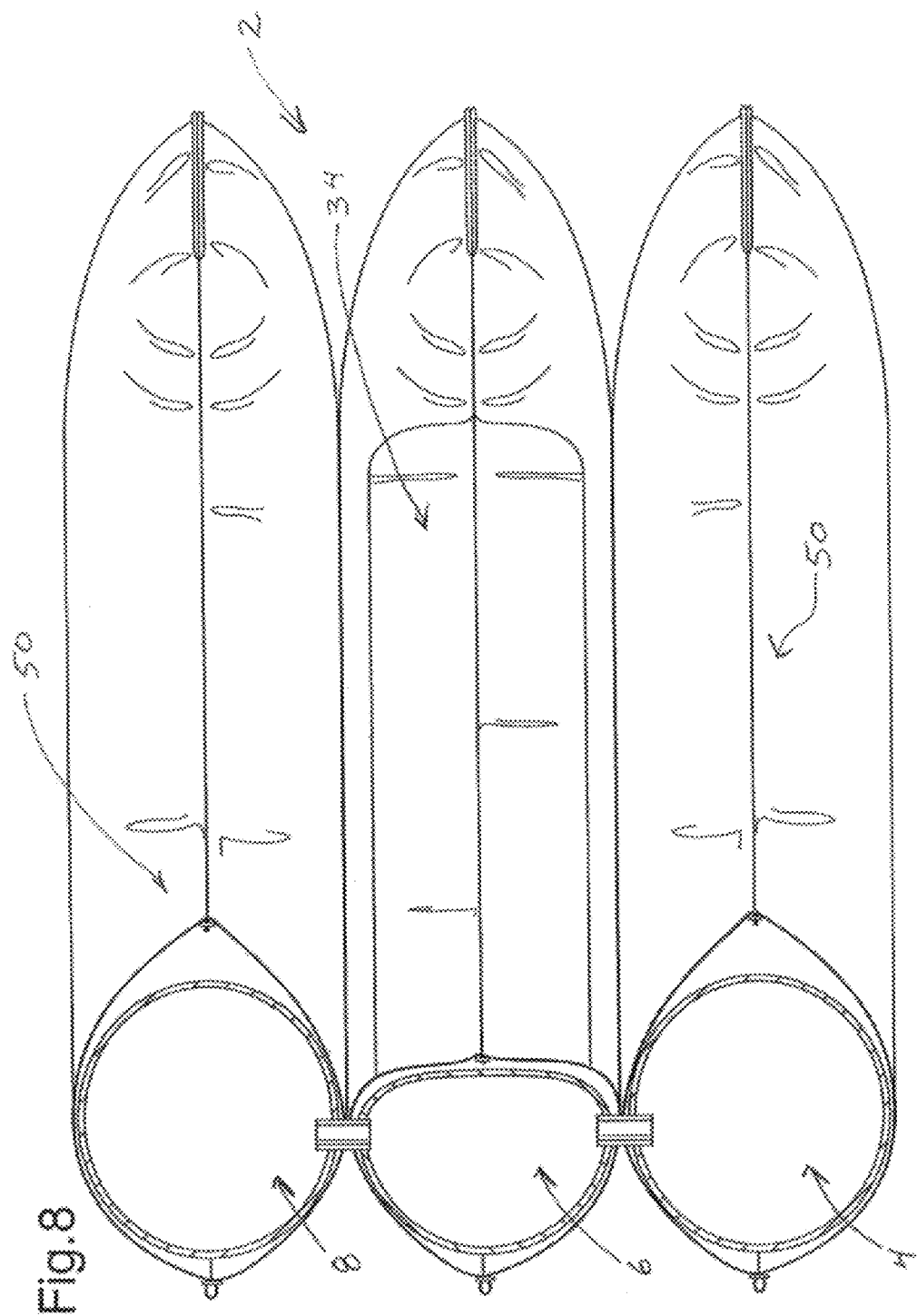

INFLATABLE CERVICAL TRACTION DEVICE

FIELD OF THE INVENTION

The present invention relates to cervical traction devices and in particular relates to such devices that are inflatable and adapted to receive a replaceable insert for removing heat from the neck region during the traction thereof.

BACKGROUND OF THE INVENTION

Inflatable traction devices for the neck of a user are available and a number of these traction devices include inflatable bladders that are applied about the neck of a user and are inflated to provide some separation between the cervical joints. These devices have been of assistance to a number of users to provide some expansion of the joints.

One of the benefits of this system is the convenience thereof allowing a user to use the device at his own convenience and to also vary the time that the device is worn.

The present invention significantly improves the utility of the cervical traction device by providing a structure where a cold pack can be inserted into the cervical device to additionally provide cooling to the neck region during the use of the cervical traction device. Such cooling reduces swelling and therefore provides a secondary effect in the treatment of any neck injuries. The pneumatic cervical traction device is adapted to accommodate a cooling pack and to modify the pressure applied in the region of the cooling pack due to a shaping of the bladder adjacent the cooling pack.

SUMMARY OF THE INVENTION

A cervical traction device according to the present invention includes an inflatable bladder shaped for application about the neck of a user and a pump for inflating and maintaining an inflated state of said bladder. The cervical traction device, on an interior surface, includes a removable therapeutic thermal pack supported in a thermal transfer position with a user's neck during use of said device.

According to an aspect of the invention, the traction device includes a releasable fastener for securing the bladder about the neck during inflation of the bladder.

According to an aspect of the invention, the inflatable bladder is shaped to define a recessed pocket sized to receive the removable therapeutic thermal pack.

In a further aspect of the invention, the bladder includes 3 distinct interconnected inflatable tubes stacked one above the other with the intermediate tube being of a reduced size to define the recessed pocket on the interior surface of the device.

According to an aspect of the invention, the device includes a separate fabric member releasably secured to the device in front of the therapeutic thermal pack that allows thermal transfer therethrough.

In a preferred aspect of the invention, the therapeutic thermal pack is elongate and is centrally disposed intermediate two opposed ends of said bladder.

In an aspect of the invention, the 3 tubes of the bladder are maintained within a cover having an enclosure for each tube with the enclosure of the intermediate tube being of reduced size to form a recessed pocket in front of the intermediate tube. The enclosure for each of the remaining tubes forms a top and bottom boundary of the recessed pocket.

In a further aspect of the invention, the enclosures of the remaining tubes include a releasable fastener for securing a separate fabric member positioned in front of the therapeutic thermal pack.

A cervical traction device, in a preferred aspect of the invention, comprises an inflatable bladder shaped for application about the neck of a user with a securement arrangement for maintaining the bladder about the neck during inflation of the bladder in combination with an arrangement for inflating and maintaining an inflated state of the bladder. The cervical traction device includes, on an interior surface thereof, an elongate recessed pocket sized to receive a removable gel pack and an elongate thermal pack is removably received in the recessed pocket in a position of thermal contact with a user's neck during traction of the neck by inflation of the device.

BRIEF DESCRIPTION OF THE DRAWINGS

Preferred embodiments of the invention are shown in the drawings, wherein:

FIG. 2 is an exploded perspective view showing the cervical traction device and the replaceable cooling pack insertable into the device;

FIG. 3 is a cross sectional device of the cervical traction device without the cold pack insert;

FIG. 4 is a view similar to FIG. 3 with the cold pack inserted in the cervical traction device;

FIG. 5 is a top view of the cervical traction device showing the top inflatable region in combination with a recessed center inflatable region adapted to receive the cold pack;

FIG. 6 is a view similar to FIG. 5 however the cervical traction device is in an inflated state;

FIG. 7 is a partial perspective cutaway view showing the cervical traction device in an inflated state with a cold pack inserted therein;

FIG. 8 shows the cervical traction device in an inflated state without the cold pack.

DETAILED DESCRIPTION OF THE PREFERRED EMBODIMENTS

Figure 1:
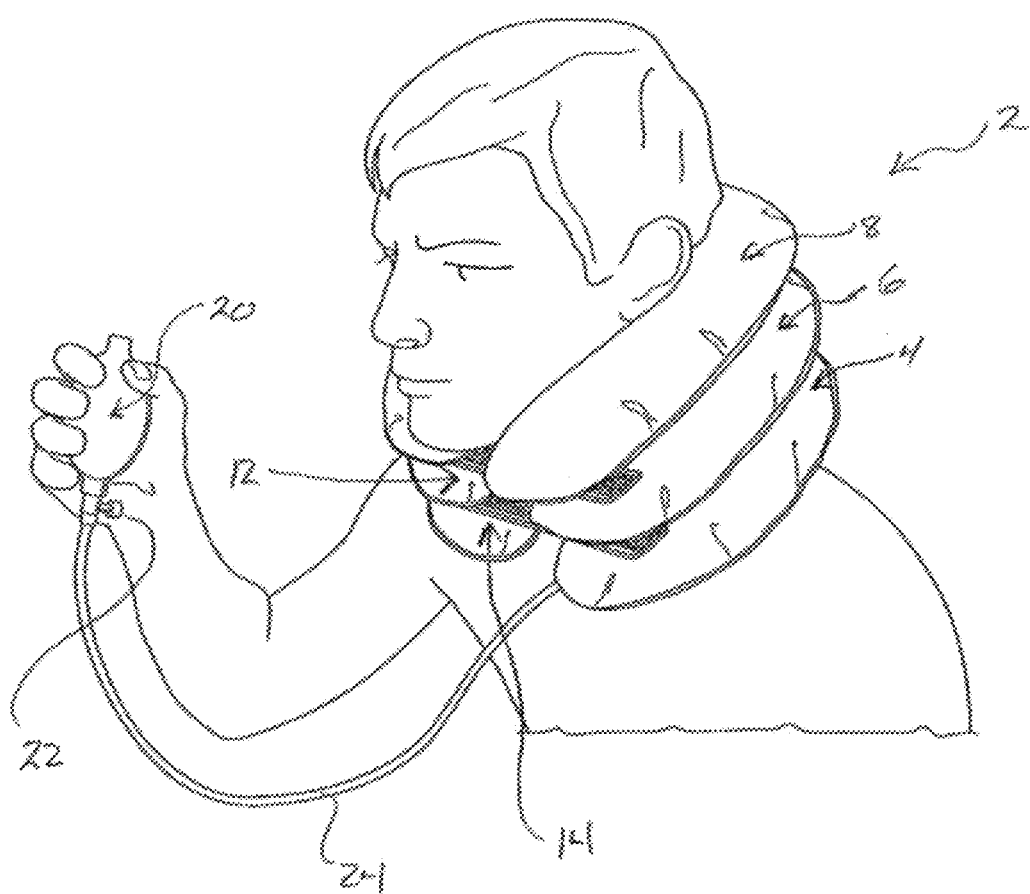
FIG. 1 is a perspective view of the cervical traction device being worn by a user.

The cervical traction device 2 preferably includes a series of inflatable regions indicated as 4, 6 and 8. These inflatable regions expand and contract by manipulation of the air pump 20 in combination with the open/close valve 22.

The traction device 2 includes front fasteners 12 and 14 for applying the device about the neck of a user essentially in a non-inflated state and the device is then inflated to apply an upward force and extension of the cervical portion of the neck. Air conduit 24 effectively connects to the inflatable bladders 4a, 6a and 8a, shown in FIG. 3. These inflatable bladders are interconnected by the connecting tubes 44. Other arrangements including a manifold can be used for inflating the bladders.

As shown in FIGS. 3, 4, 5 and 6, the inflatable bladder 6a is of a smaller size on the interior surface 11 of the cervical traction device 2. This reduction in size forms a recessed pocket 34 that is sized for receiving the replaceable cold pack 30. This cold pack can be taken from the freezer and inserted into the recessed pocket 34 and heat is removed from the neck surface of the user adjacent the spinal column. This will reduce swelling in the region and the cervical traction device when inflated causes expansion of the particular joints.

Although a cold pack 30 is described, other therapeutic packs can be used including a gel heat applying pack or other known therapeutic packs typically for applying or removing heat with or without a moisture component.

As shown in FIGS. 5 and 6, the inflatable bladder 6a is of a reduced width and as such each of the inflatable bladders 4a and 8a extend to the position as generally shown by bladder 8a in the Figures. When the cervical traction device 2 is inflated as shown in FIG. 6, the recessed pocket 34 reduces in size, however there still is substantial space to retain the cold pack 30 that is less compressible. The cold pack is then pressed by the inflated bladder against the user's neck and is pressed either side of the spine. The user can vary the inflation of the device to achieve a desired extension of the cervical spine in combination with a pressure force pushing the cold pack against the neck of the user.

Preferably, as shown in FIG. 7, a removable cover 40 is attached either side of the central inflatable region 6 and this cover separates the outer surface of the cold pack from the skin of the user. The cover is removable to allow for convenient cleaning thereof and to also allow convenient insertion of the cold pack into the recess 34.

As shown in FIGS. 3 and 4, the inflatable regions 4, 6 and 8 include a sewn cover 50 which includes essentially three sleeves for receiving the inflatable bladders 4a, 6a and 8a, in the cervical traction device and the user does not have access to these bladders. The recessed pocket 34 is exterior to the cover 50 that is also shaped to conform with the configuration of the smaller inflatable bladder 6a. As seen in FIGS. 7 and 8 the cover 50 is shaped to closely fit the bladder 6 and define the recessed pocket 34. In FIG. 8 the bladder 6 is further reduced in size to increase the size of the recessed pocket 34.

It has been found that this particular cervical traction device that is able to apply heat or cold to the neck region of the user during the expansion of the neck, is advantageous and beneficial. The provision of adapting the central inflatable bladder to define a recessed region between the upper inflatable bladder and a lower inflatable bladder applies heat or cold to the user at a central region and effectively cools or heats a somewhat larger area. The therapeutic pack located between upper and lower bladders 4a and 8a is somewhat isolated by the bladders and concentrates the treatment to a desired region.

As can be appreciated, if the user does not wish to apply heat or cold in a particular session the cold pack can remain in place if it is effectively at room temperature which would be close to the skin temperature of the user. Even if the cold pack is removed the central inflatable bladder 6a will partially expand into the recessed area and upwardly to provide the desired traction. Recessing of the therapeutic pack provides the same fit or comfort of the traction device. The pressure exerted by the therapeutic pack on the neck of the user is similar to the pressure exerted by adjacent bladders.

The recessing in the middle bladder is preferably quite substantial (40 to 60% of the depth of the upper or lower bladders). With this recessed arrangement the recessed bladder and therapeutic pack cooperate to provide traction, temperature therapy and generally consistent pressure (for comfort to the user). Without the recess, the traction device does not sit in the preferred position and the therapeutic pack provides an excessive pressure point or ridge rendering the traction device less effective.

In a modified embodiment both the intermediate bladder 6a and the lower bladder 4a are recessed to receive a therapeutic pack. The upper bladder remains without a recess to provide effective engagement of the head to provide traction. The lower bladder 4a preferably is not recessed in the area where the bladder engages the shoulders of a user. One or more therapeutic packs can be used and the shape thereof will provide an appropriate fit in the recessed pockets. It is preferable that the lower bladder when inflated engages the neck of the user beneath the therapeutic pack.

With the present structure a series of bladders and covers cooperate to releasably receive a therapeutic pack on an interior surface for thermal contact with the neck of a user when the bladders are inflated. The preferred structure uses 3 bladders with a center bladder at the interior surface of a reduced depth to define a pocket or cavity for the therapeutic pack. Other arrangements are possible to desirably position and return the therapeutic pack or packs at the desired position will still providing the traction device to operate in its intended manner.

Figure 9:
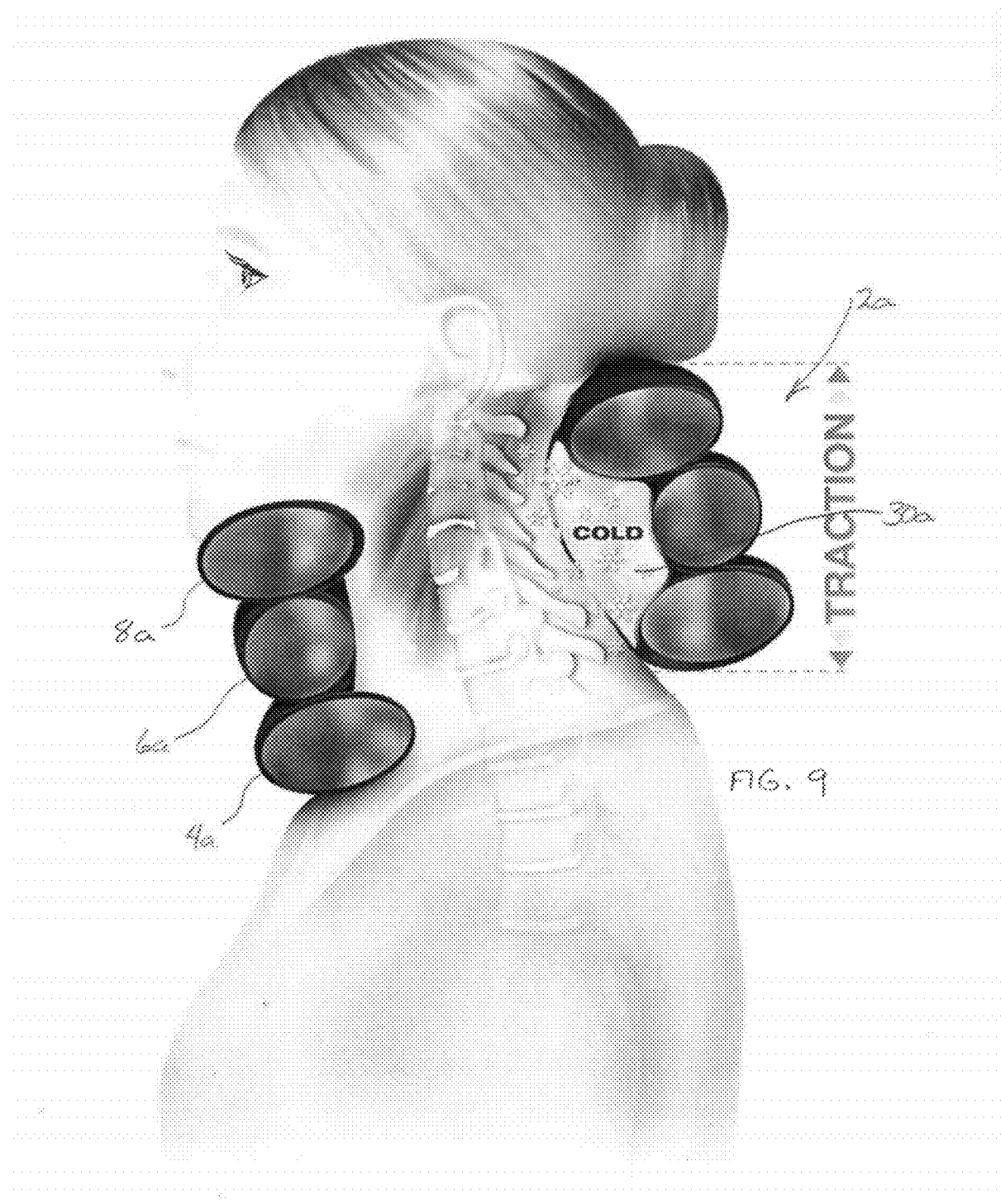
FIG. 9 is a partial perspective cutaway view of an alternate embodiment.

In the alternate traction 2a of FIG. 9 the inflatable regions 4a, 6a and 8a extend forwardly beneath a user's chin as generally shown. As in the earlier embodiment the inflatable region 6a is of reduced size.

In the embodiment shown, region 6a beneath the chin of a user has a gap relative to the inside edges of upper region 8a and lower region 4a. This additional space exerts less pressure on the wearer's neck at the adam's apple region. The reduction in size and offsetting still allows effective traction while being more comfortable to use.

A further feature of the traction device is the accommodation of the thermal pads 30a and the concentration thereof adjacent to the inflatable region 6a. This arrangement provides additional thermal mass in the center region of the inflatable regions for cooling or heating of a user's neck. With this arrangement the desired cooling or heating effect will remain effective for an additional time and be applied to the desired area. The upper and lower regions when inflated assist in limiting the flow of the gel material upwardly or downwardly.

A number of embodiments of the present invention have been described herein in detail, however it will be appreciated by those skilled in the art, that further variations are possible that utilize the principles disclosed herein.

The embodiments of the invention in which an exclusive property or privilege is claimed are defined as follows:

1. A cervical traction device comprising:
   an inflatable bladder shaped for application about a neck of a user;
   an arrangement for inflating and maintaining an inflated state of said inflatable bladder;
   said cervical traction device including on an interior surface, a removable therapeutic thermal pack supported in a thermal transfer position with the user's neck during use of said cervical traction device; and
   wherein said inflatable bladder is shaped to define a recessed pocket in an exterior surface of said bladder sized to receive said removable therapeutic thermal pack; and
   wherein said bladder includes three distinct interconnected inflatable tubes stacked one above the other with an intermediate tube being of a reduced size to define said recessed pocket on said interior surface of said cervical traction device.

2. A cervical traction device as claimed in claim 1 wherein said cervical traction device includes a separate fabric member releasably secured to said cervical traction device in front of said therapeutic thermal pack that allows thermal transfer therethrough.

3. A cervical traction device as claimed in claim 2 wherein said therapeutic thermal pack is elongate and is centrally disposed intermediate two opposed ends of said bladder.

4. A cervical traction device as claimed in claim 1 wherein said three tubes are maintained within a cover having an enclosure for each tube; and wherein said enclosure of said intermediate tube is of reduced size to form a recessed pocket in front of said intermediate tube with said enclosure for each of the remaining tubes forming a top and bottom boundary of said recessed pocket.

5. A cervical traction device as claimed in claim 4 wherein said enclosures of said remaining tubes include a releasable fastener for securing the separate fabric member positioned in front of said therapeutic thermal pack.

6. A cervical traction device as claimed in claim 1 wherein said cervical traction device includes a releasable fastener configured for maintaining the inflatable bladder about the neck during inflation of the inflatable bladder.

7. A cervical traction device as claimed in claim 1 wherein said inflation arrangement is a pump and valve arrangement connected to said inflatable bladder.

8. A cervical traction device comprising:
an inflatable bladder shaped for application about a neck of a user with a securement arrangement for maintaining the bladder about the neck during inflation of the bladder;
an arrangement for inflating and maintaining an inflated state of said bladder;
said cervical traction device including on an interior surface thereof an elongate recessed pocket in an exterior surface of said bladder; and
an elongate thermal pack removably received in said recessed pocket in a position configured to provide thermal contact with the user's neck during traction of the neck by inflation of said bladder; and
wherein said inflatable bladder has an upper region, a middle region and a lower region with said middle region on an inside edge thereof being outwardly offset relative to an inside edge of said upper and lower regions;
said middle region being of reduced size and accommodating at said inside edge said thermal pack generally between said upper and lower region and within said elongated recessed pocket.

\* \* \* \* \*